United States Patent
Kim et al.

(10) Patent No.: US 9,784,912 B2
(45) Date of Patent: Oct. 10, 2017

(54) OPTIC FIBER WITH CARBON NANO-STRUCTURE LAYER, FIBER OPTIC CHEMICAL SENSOR AND METHOD FOR FORMING CARBON NANO-STRUCTURE LAYER IN FIBER CORE

(75) Inventors: Tae-sung Kim, Suwon-si (KR); Atul Kulkarni, Suwon-si (KR); Jaeboong Choi, Yongin-si (KR); Hyeong Keun Kim, Hwaseong-si (KR); Young Jin Kim, Seoul (KR); Byung Hee Hong, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 13/442,026

(22) Filed: Apr. 9, 2012

(65) Prior Publication Data
US 2012/0288227 A1 Nov. 15, 2012

Related U.S. Application Data

(63) Continuation of application No. PCT/KR2010/006894, filed on Oct. 8, 2010.

(30) Foreign Application Priority Data

Oct. 9, 2009 (KR) .................. 10-2009-0096439

(51) Int. Cl.
*G02B 6/02* (2006.01)
*G01N 21/77* (2006.01)

(52) U.S. Cl.
CPC ....... *G02B 6/0229* (2013.01); *G01N 21/7703* (2013.01); *G01N 2021/7713* (2013.01)

(58) Field of Classification Search
USPC ........................................ 356/445
See application file for complete search history.

(56) References Cited

U.S. PATENT DOCUMENTS

| | | | | |
|---|---|---|---|---|
| 5,327,225 A * | 7/1994 | Bender et al. | ................ | 356/445 |
| 5,359,681 A * | 10/1994 | Jorgenson et al. | ............. | 385/12 |
| 5,822,073 A * | 10/1998 | Yee et al. | ...................... | 356/445 |
| 6,457,350 B1 | 10/2002 | Mitchell | | |
| 6,869,581 B2 * | 3/2005 | Kishi et al. | ................ | 423/447.6 |
| 8,139,617 B2 * | 3/2012 | Song | .............................. | 372/18 |

(Continued)

FOREIGN PATENT DOCUMENTS

EP   1918262 A1   5/2008

OTHER PUBLICATIONS

Dresselhaus et al., "Science of fullerenes and carbon nanotubes", Academic Press, San Diego, 1996, pp. 756-869.*

(Continued)

*Primary Examiner* — Shawn Decenzo
(74) *Attorney, Agent, or Firm* — NSIP Law

(57) ABSTRACT

The invention relates to an optic fiber having a core in which carbon nano-structures are formed at a predetermined locus, a fiber optic chemical sensor using the optic fiber, and a method of forming the carbon nano-structure layer in the core of the optic fiber. The invention utilizes gas refractive index and the adsorption sensitivity of particles on the surface of the carbon nano-structure layer, and uses the carbon nano-structure layer in the core of the optic fiber as a sensor for particles of gas, liquid and the like.

22 Claims, 13 Drawing Sheets

(56) References Cited

U.S. PATENT DOCUMENTS

| | | | |
|---|---|---|---|
| 2003/0044608 A1* | 3/2003 | Yoshizawa et al. | 428/398 |
| 2010/0021708 A1* | 1/2010 | Kong et al. | 428/220 |
| 2011/0048625 A1* | 3/2011 | Caldwell et al. | 156/233 |
| 2012/0039344 A1* | 2/2012 | Kian | H01S 3/1118 372/6 |

OTHER PUBLICATIONS

Geim et al., "The Rise of Graphene", Nature Materials, vol. 6, 2007, p. 183-191.*

Maffucci et al., "Graphene, Carbon Nanotubes, and Nanostructures Techniques and Applications", CRC Press 2013, Chapter 1, pp. 1-24.*

Goncalves, Gil, et al. "Surface modification of graphene nanosheets with gold nanoparticles: the role of oxygen moieties at graphene surface on gold nucleation and growth." Chemistry of Materials 21.20 (2009): 4796-4802.*

Song, Y.W., et al., Single-walled carbon nanotubes for high-energy optical pulse formation, Applied Physics Letters 92, Jan. 16, 2008, 3 Pages.

International Search report issued Jun. 30, 2011, in counterpart International Application No. PCT/KR2010/006894 (6 Pages, including English translation).

\* cited by examiner

FIG. 1
(a)
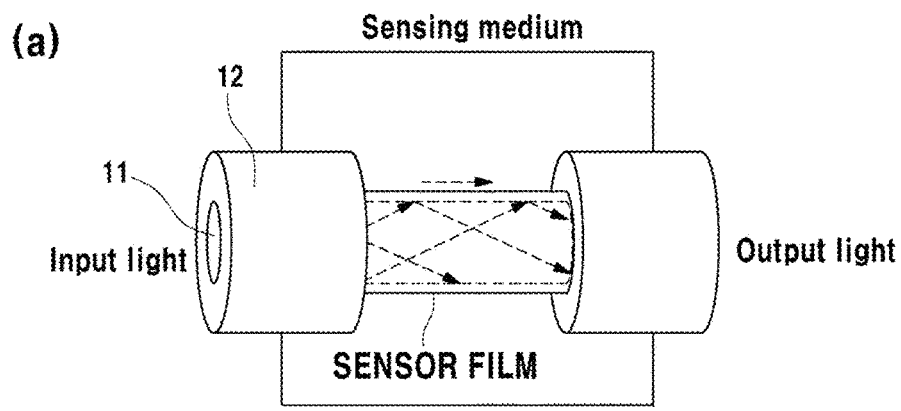
(b)
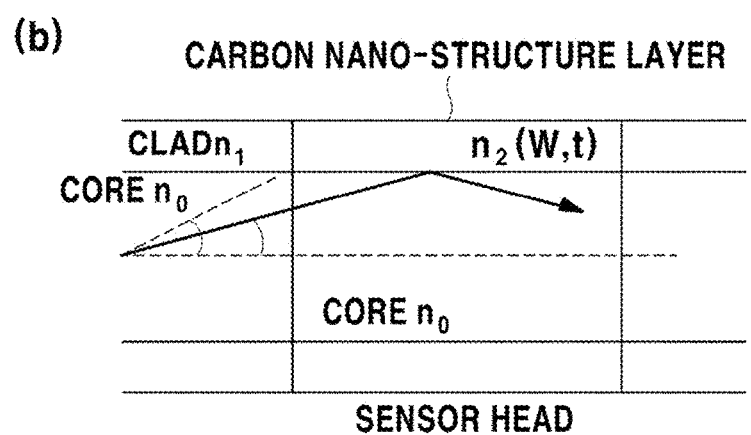
(c)
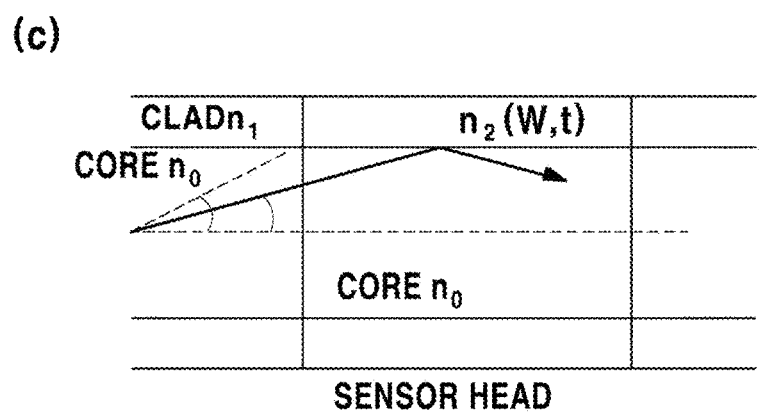

FIG. 2
(a) 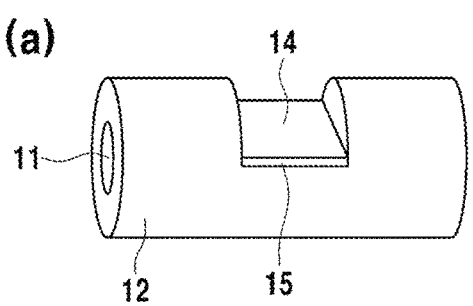
(b) 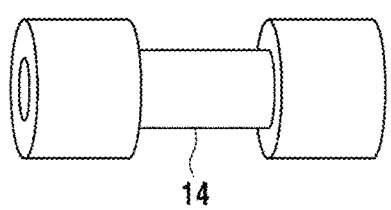
(c) 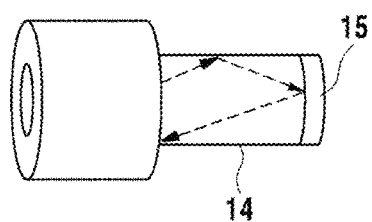
(d) 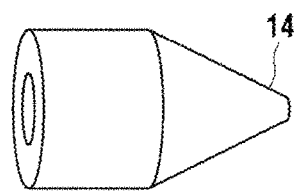
(e) 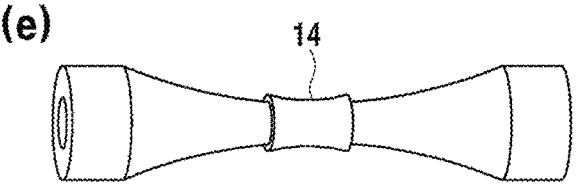

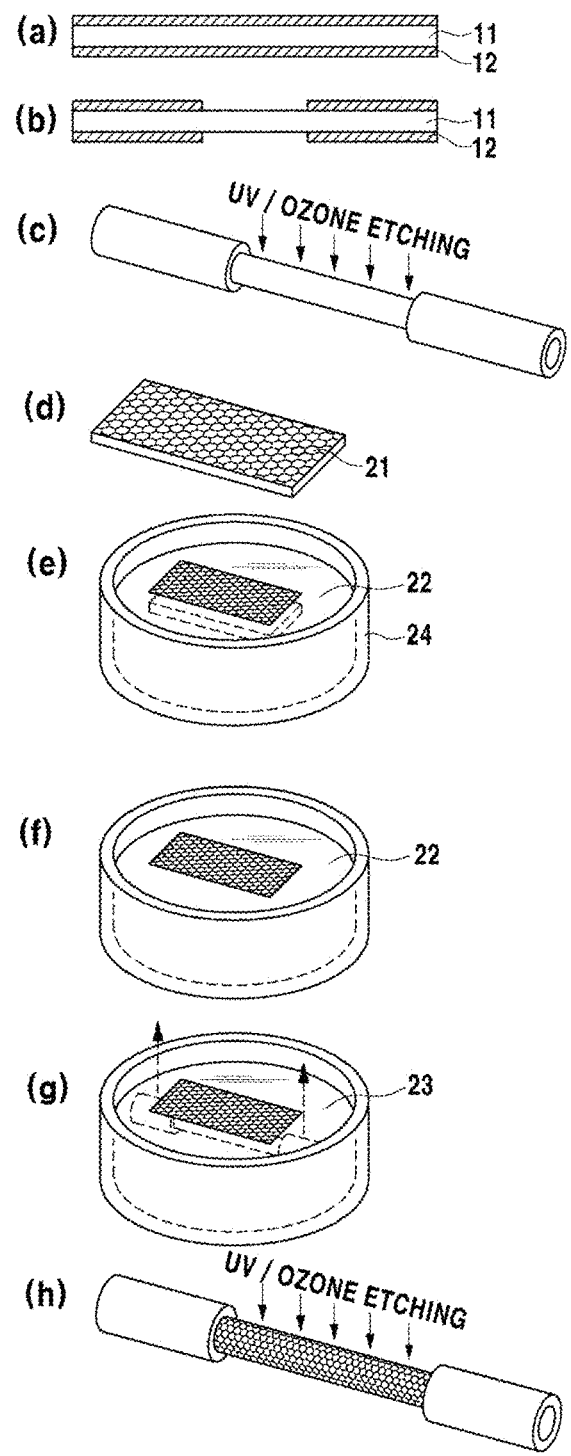

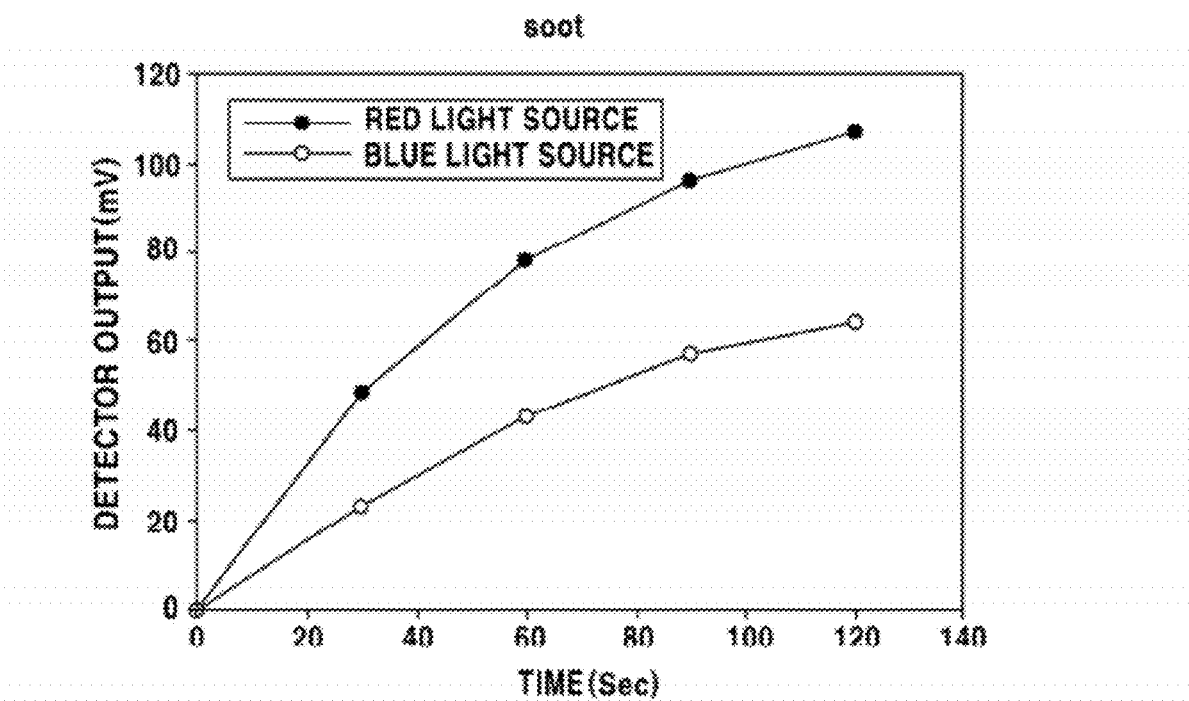

OPTIC FIBER WITH CARBON NANO-STRUCTURE LAYER, FIBER OPTIC CHEMICAL SENSOR AND METHOD FOR FORMING CARBON NANO-STRUCTURE LAYER IN FIBER CORE

CROSS-REFERENCE TO RELATED APPLICATION

This application is a Continuation of International Application No. PCT/KR2010/006894 filed on Oct. 8, 2010, which claims the benefits of Korean Patent Application No. 10-2009-0096439 filed on Oct. 9, 2009. The entire disclosure of the prior application is incorporated herein by reference in its entirety.

TECHNICAL FIELD

The present disclosure relates to an optic fiber having a core in which a carbon nano-structure layer is formed at a predetermined locus, an optic fiber chemical sensor including the optic fiber, and a method of forming the carbon nano-structure layer on the core of the optic fiber. To be specific, the present disclosure relates to an optic fiber having a core in which there is formed a carbon nano-structure layer of which a surface refractive index reacts sensitively to adsorption of gases or particles, an optic fiber chemical sensor including the optic fiber, and a method of forming the carbon nano-structure layer on the core of the optic fiber, the method including removing a sheath and a jacket from a predetermined locus of the optic fiber and forming the carbon nano-structure layer on the exposed core at the predetermined locus of the optic fiber.

BACKGROUND ART

Optic fibers receive less interference from the external environment and have a low rate of information loss. Thus, the optic fibers are widely used in various fields for transmitting or detecting information of a general communications network, a cable broadcasting network, and various automatic devices. A sensor using the optic fibers functions as a detector by using elasticity depending on temperature or pressure, a phase difference of light or the Doppler effect. To be specific, the sensor is used for many purposes such as a temperature sensor, a pressure sensor, a gyroscope, a speedometer, a windvane, and a gas leak sensor. In particular, a sensor used for detecting gases, compounds, biomolecules, and the like has received a lot of attention for a long time and a lot of research thereof has been published. The gas sensor has been used in various fields such as chemistry, pharmaceuticals, environment, and medical treatment and is expected to be researched further in the future. As social demands such as environmental preservation and safety management increase, performance and specifications required for the gas sensor have been advanced.

In response to such demands for the gas sensor of high sensitivity and high performance, a lot of research on new materials for the gas sensor has been carried out and applications of new materials of high sensitivity to the gas sensor have been made.

DISCLOSURE OF THE INVENTION

Problems to be Solved by the Invention

In view of the foregoing, the present disclosure provides an optic fiber having a core in which there is formed a carbon nano-structure layer of which a surface refractive index reacts sensitively to adsorption of gases or particles, an optic fiber chemical sensor including the optic fiber, and a method of forming the carbon nano-structure layer on the core of the optic fiber for fabricating the optic fiber.

However, the problems to be solved by the present disclosure are not limited to the above description and other problems can be clearly understood by those skilled in the art from the following description.

Means for Solving the Problems

To solve the above-described problems, in accordance with an aspect of the present disclosure, there is provided an optic fiber including a carbon nano-structure layer formed on a core at a predetermined locus of the optic fiber.

In accordance with another aspect of the present disclosure, there is provided an optic fiber chemical sensor including the optic fiber, wherein a sensing part in the optic fiber chemical sensor includes the carbon nano-structure layer formed on the core at the predetermined locus of the optic fiber.

In accordance with still another aspect of the present disclosure, there is provided a method for forming a carbon nano-structure layer on a core of an optic fiber, the method including: removing a sheath and a jacket from a predetermined locus of the optic fiber to expose the core of the optic fiber; and forming the carbon nano-structure layer on the core of the optic fiber.

Effect of the Invention

In accordance with the present disclosure, it is possible to fabricate an optic fiber including a carbon nano-structure layer formed on a core at a predetermined locus of the optic fiber and an optic fiber sensor of remarkably improved sensitivity using the optic fiber.

In the carbon nano-structure layer of the optic fiber sensor, since a surface refractive index reacts sensitively to adsorption of a gas or a particles, the carbon nano-structure layer can be widely used in various fields such as semiconductor and environmental technology for controlling and sensing a gas and particle (aerosols, nano particles, and the like), monitoring environmental pollution, analyzing chemical composition or monitoring $NO_x$.

Further, in accordance with the method of forming the carbon nano-structure layer on the core of the optic fiber, the carbon nano-structure layer is bonded to or coated on an exposed locus of the optic fiber, so that the optic fiber chemical sensor including the carbon nano-structure layer can be manufactured effectively.

BRIEF DESCRIPTION OF THE DRAWINGS

FIG. 1 shows a principle of an optic fiber sensor;

FIG. 2 shows optic fiber sensors manufactured in accordance with various illustrative embodiments of the present disclosure;

FIG. 3 provides a manufacturing process of an optic fiber coated with a carbon nano-structure layer and an optic fiber sensor in accordance with an example of the present disclosure;

FIG. 8 provides a graph showing sensitivity for soot when a red light source and a blue light source are individually used in an optic fiber sensor in accordance with an example of the present disclosure;

BEST MODE FOR CARRYING OUT THE INVENTION

Figure 4A:
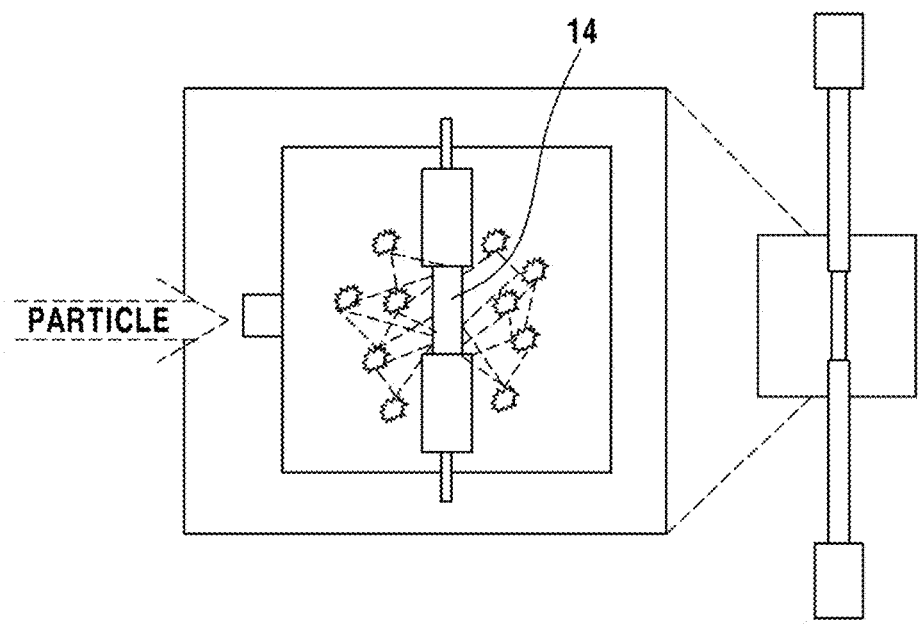
FIGS. 4A and 4B provide a schematic view and an image of an experimental system including an optic fiber sensor in accordance with an example of the present disclosure.

Hereinafter, illustrative embodiments and examples of the present disclosure will be described in detail with reference to the accompanying drawings so that the present disclosure may be readily implemented by those skilled in the art.

However, it is to be noted that the present disclosure is not limited to the illustrative embodiments and examples but can be embodied in various other ways. In drawings, parts irrelevant to the description are omitted for the simplicity of explanation, and like reference numerals denote like parts through the whole document.

In accordance with an aspect of the present disclosure, there is provided an optic fiber including a carbon nano-structure layer formed on a core at a predetermined locus of the optic fiber.

In accordance with an illustrative embodiment of the present disclosure, the carbon nano-structure layer may contain a material selected from the group consisting of, but not limited to, graphene, graphite oxide, a carbon nanotube (CNT), and combinations thereof.

In accordance with an illustrative embodiment of the present disclosure, the core of the optic fiber may contain one or more materials selected from the group consisting of, but not limited to, glass, plastic, and a polymer.

In accordance with an illustrative embodiment of the present disclosure, the optic fiber may include, but is not limited to, a multimode optic fiber.

In accordance with an illustrative embodiment of the present disclosure, a protective film may be further included by forming on the carbon nano-structure layer. The protective film is formed of a material that protects a surface of the carbon nano-structure layer from pollution and allows to sense signals on the surface of the carbon nano-structure layer without difficulty in forecasting a refractive index. A non-limited example of the protective film includes a protective film containing a polymer including porous nano holes.

In accordance with an illustrative embodiment of the present disclosure, the core, where the carbon nano-structure layer formed, at the predetermined locus of the optic fiber may have a flat surface or a curved surface.

In accordance with another aspect of the present disclosure, there is provided an optic fiber chemical sensor including the optic fiber. In the optic fiber chemical sensor, a sensing part in the optic fiber chemical sensor includes the carbon nano-structure layer formed on the core at the predetermined locus of the optic fiber.

In accordance with an illustrative embodiment of the present disclosure, the optic fiber chemical sensor may include a light source; a light detector; and the optic fiber positioned between the light source and the light detector. The light source may include light sources from all ranges of ultra-violet (UV), visible (VIS) or infrared (IR) light.

In accordance with an illustrative embodiment of the present disclosure, the optic fiber chemical sensor may detect a target material to be sensed by using a change in a photorefractive index caused by a change in a thickness of the carbon nano-structure layer included in the sensing part.

In accordance with an illustrative embodiment of the present disclosure, the carbon nano-structure layer included in the sensing part of the optic fiber chemical sensor has a surface refractive index that reacts sensitively to adsorption of a gas or a particle, and, thus, the carbon nano-structure layer can be widely used in various fields such as semiconductor and environmental technology for controlling and sensing a gas and a particle (aerosols, nano particles, and the like), monitoring environmental pollution, analyzing chemical composition or monitoring $NO_x$. By way of example, the optic fiber chemical sensor can detect target materials having various chemical components in a gas, liquid or particle form but it is not limited thereto. The optic fiber chemical sensor can detect a compound gas or liquid selected from the group consisting of, but not limited to, $H_2$, CO, $CO_2$, $O_2$, $NO_x$), DMMP, $CH_4$, $NH_3$, $CH_3OH$, LPG, $H_2S$, benzene, $CH_3SH$, toluene, VOC and combinations thereof.

In accordance with another aspect of the present disclosure, there is provided a method for forming an optic fiber chemical sensor that includes the optic fiber, the method including removing a sheath and a jacket from a predetermined locus of the optic fiber to expose a core of the optic fiber; forming a sensing part including a carbon nano-structure layer on the exposed core at the predetermined locus of the optic fiber; and positioning the optic fiber including the sensing part between a light source and a light detector.

In accordance with an illustrative embodiment of the present disclosure, the method for forming the optic fiber chemical sensor may further include surface treating the exposed core of the optic fiber with UV or plasma.

In accordance with an illustrative embodiment of the present disclosure, the sensing part may be formed by exposing the core at the predetermined locus by removing the sheath and the jacket from the predetermined locus of the optic fiber; floating the carbon nano-structure layer on a surface of distilled water; and contacting the exposed core of the optic fiber with the floated carbon nano-structure layer to transfer the carbon nano-structure layer onto the exposed core.

In accordance with an illustrative embodiment of the present disclosure, the sensing part may be formed by exposing the core at the predetermined locus by removing the sheath and the jacket from the predetermined locus of the optic fiber; floating the carbon nano-structure layer on a surface of distilled water; transferring the carbon nano-structure layer onto a stamper containing elastomer; and transferring the carbon nano-structure layer onto the exposed core by pressing the carbon nano-structure layer transferred on the stamper to the exposed core of the optic fiber. According to this method, even if the core of the optic fiber does not have a flat surface, it is possible to easily transfer the carbon nano-structure layer onto the core.

In accordance with still another aspect of the present disclosure, there is provided a method for forming a carbon nano-structure layer on a core of an optic fiber, the method including forming the carbon nano-structure layer on the core exposed by removing a sheath and a jacket from a predetermined locus of the optic fiber.

In accordance with an illustrative embodiment of the present disclosure, the method for forming a carbon nano-structure layer in the core of the optic fiber may include exposing the core at the predetermined locus by removing the sheath and the jacket from the predetermined locus of the optic fiber; floating the carbon nano-structure layer on a surface of distilled water; and contacting the exposed core of the optic fiber with the floated carbon nano-structure layer to transfer the carbon nano-structure layer onto the exposed core.

In accordance with an illustrative embodiment of the present disclosure, the method for forming a carbon nano-structure layer on the core of the optic fiber may include exposing the core at the predetermined locus by removing the sheath and the jacket from the predetermined locus of the optic fiber; floating the carbon nano-structure layer on a surface of distilled water; transferring the carbon nano-structure layer onto a stamper containing elastomer; and transferring the carbon nano-structure layer onto the exposed core by pressing the carbon nano-structure layer transferred on the stamper to the exposed core of the optic fiber.

In accordance with an illustrative embodiment of the present disclosure, the method for forming the carbon nano-structure layer on the core of the optic fiber may include coating the exposed core by pressing the stamper along a circumference of the exposed core.

In accordance with an illustrative embodiment of the present disclosure, in the method for forming the carbon nano-structure layer on the core of the optic fiber, a graphene layer formed by chemical vapor deposition with control of its area and thickness may be used.

Hereinafter, illustrative embodiments and examples of an optic fiber having a core in which a carbon nano-structure layer is formed at a predetermined locus, an optic fiber chemical sensor including the optic fiber, and a method of forming the carbon nano-structure layer on the core of the optic fiber for manufacturing the optic fiber will be explained in detail with reference to accompanying drawings. However, the present disclosure is not limited thereto.

FIG. 1 shows a principle of an optic fiber sensor. In the optic fiber sensor coated with a carbon nano-structure layer in accordance with the present disclosure, if pollutant particles or gas particles adhere to the carbon nano-structure layer, a change in a photorefractive index is occurred and a light detector measures such a change. In this way, the optic fiber sensor functions as a sensor. FIGS. 1(b) and 1(c) show paths of light depending on refractive indexes of a core $n_0$, a clad $n_1$, and a carbon nano-structure layer $n_2$. FIG. 1(b) shows that if $n_0$ is low and $n_2$ is greater than $n_1$, light is leaked to the outside of the carbon nano-structure layer. FIG. 1(c) shows that if $n_0$ is high and $n_2$ is smaller than $n_1$, light is refracted into the core of the optic fiber.

FIG. 2 shows optic fiber sensors manufactured in accordance with various illustrative embodiments of the present disclosure. Referring to FIG. 2, a predetermined locus of a core 11 of an optic fiber can be exposed in various ways, and a carbon nano-structure layer is formed at the predetermined locus to serve as a sensing part. Herein, a metal layer 15 in accordance with an illustrative embodiment serves as a mirror that regularly reflects a light source, thereby refracting at the sensing part 14 of the optic fiber sensor (i.e. it functions to increase signal sensitivity).

FIG. 3 provides a manufacturing process of an optic fiber having a core in which a carbon nano-structure layer is formed at a predetermined locus and an optic fiber sensor including the optic fiber in accordance with an example of the present disclosure. In order to manufacture an optic fiber sensor, a light source (not illustrated) and a light detector (not illustrated) may be further provided. The light source may include light sources from all ranges of UV, VIS or IR. Then, with respect to an optic fiber (see FIG. 3(a)), a typical optic fiber includes a core 11 having a diameter of about 980 micrometers, a clad 12 having a diameter of about 20 micrometers and covering the core 11, and a jacket (not illustrated) having a diameter of about 2.2 millimeters and covering the clad 12. Herein, the core of the optic fiber may include one or more materials selected from the group consisting of, but not limited to, glass, plastic, and a polymer. Further, the optic fiber may include, but is not limited to, a multimode optic fiber. Furthermore, the core, where the carbon nano-structure layer formed, at the predetermined locus of the optic fiber may have a flat surface or a curved surface.

A typical plastic optic fiber (POF) includes a core 11 made of resin and a clad 12 made of a fluorescent polymer. The plastic optic fiber can be cut into a desired length by a sharp cutter for use.

FIG. 3(b) is a cross sectional view of a plastic optic fiber cut into the same length as a detecting part. The detecting part can be prepared by using a device that peels off a sheath of the jacket (not illustrated). When the jacket (not illustrated) is peeled off, the clad 12 and the core 11 remain. Thereafter, both ends of the plastic optic fiber can be planarized with a fine sandpaper sheet and the like. The planaraziation process is very important for connection with an optic signal detector. Typically, in the planaraziation process, the optic fiber is rotated on the sandpaper sheet until a desired degree of planarization can be obtained. Then, the clad 12 may be removed. The clad 12 of the optic fiber is chemically treated with a solvent such as N,N-dimethylformamide, and a piece of clean cloth is soaked in the solvent and used to rub the clad 12 of the optic fiber. Since the clad 12 is weaken by the chemical solvent, when the optic fiber is put in the clean cloth and puled out, only the clad 12 may be removed and the core 11 can be exposed. When the jacket (not illustrated) and the clad 12 are removed, good care should be taken not to damage the core 11. The exposed locus of the core 11 serves as the sensing part 14 of the optic fiber sensor and can be cleaned with double distilled water and a nitrogen gas. Then, the optic fiber where a carbon nano-structure layer is to be formed is accommodated in a vacuum chamber, so that it is possible to prevent additional pollution at a reaction area. Here, before the sensing part 14 of the optic fiber sensor is coated with or bonded to the carbon nano-structure layer, a UV/ozone treatment (or a plasma surface treatment) may be performed to a surface of the sensing part 14 as a pre-treatment (FIG. 3(c)).

Thereafter, a carbon nano-structure layer 21 to be coated on the sensing part 14 of the optic fiber sensor may be prepared. The carbon nano-structure layer 21 may include a material selected from the group consisting of, but not limited to, graphene, graphite oxide, a carbon nano tube (CNT), and combinations thereof.

The carbon nano-structure layer 21, for example, a graphene layer can be formed in various thicknesses through the following process. By way of example, in case of the graphene layer, under conditions for synthesizing high quality graphene, graphene layers of various thicknesses can be prepared and used in a probe of a plastic optic fiber sensor. By way of example, by using a thermal evaporator, an e-beam evaporator, a sputter or an electro-plating method, one or more metals or alloys serving as a catalyst for forming graphene and selected from the group consisting of Ni, Co, Fe, Pt, Au, Al, Cr, Cu, Mg, Mn, Mo, Rh, Si, Ta, Ti, W, U, V, Zr, brass, bronze, stainless steel, and Ge are deposited on a substrate in a thin film form, so that a metal catalyst layer can be formed. Herein, the substrate may include various foil/sheets such as Ni, stainless steel, Cu, and the like in a metal foil form as well as $SiO_2$/Si. Further, the substrate and the metal catalyst layer may be patterned. Then, the prepared substrate is put in a chemical vapor deposition chamber and heated in an argon atmosphere up to about 1000° C. The deposited metal catalyst layer may be put in a reactor and heated while being supplied with a hydrogen gas, so that an oxide layer and impurities can be removed from the metal catalyst layer. The metal catalyst layer can be reduced with the hydrogen gas, so that it is possible to obtain the catalyst layer suitable for forming large-sized graphene. Thereafter, while the metal catalyst layer is heated at a high temperature, a gas containing carbon ($CH_4$, $C_2H_2$, $C_2H_4$, CO, $C_2H_5OH$, and the like) may be supplied into the reactor together with an Ar gas or a He gas. In case of using a plasma-enhanced (PE) CVD method in which after a vacuum level is increased, an electric field is applied to generate plasma, a growth temperature can be reduced. If the metal catalyst layer is rapidly cooled after a sufficient amount of carbon is absorbed into the metal catalyst layer, carbon is separated from the metal catalyst layer such as a Ni layer and crystallized on the surface. Depending on the amount of carbon, graphene films of various number of layers can be formed. A cooling temperature can be optimized by using argon, so that under cooling conditions for minimizing defects and amorphous carbon, the graphene films can be formed (FIG. 3(d)).

A thickness of a graphene film pattern formed as described above can be adjusted by varying a reaction time, a thickness of the metal catalyst layer, and a cooling rate. When the reaction time is shorter and the thickness of the metal layer is smaller, a thickness of the graphene film can be smaller. Otherwise, by irradiating UV of about several tens of W to the formed graphene film at room temperature/normal pressure, the thickness of the graphene film can be further adjusted.

The formed graphene film pattern can be separated from the metal catalyst layer by using various acids or HF, HOE, $FeCl_3$, and $Fe(NO_3)_3$ and can be transferred to various substrates.

To be more specific, the graphene film, in particular, the carbon nano-structure layer 21 formed as described above put in a container 24 filled with various acid solutions 22 or HF, HOE, $Fe(NO_3)_3$ or iron(III) chloride ($FeCl_3$) each serving as an oxidation/etching solution, so that the metal catalyst layer can be removed (FIG. 3(e)). In an oxidation-reduction process, the metal catalyst layer is etched gradually in a neutral pH range and a gaseous material is not generated. Therefore, a gas collector for removing a gas is not needed. After a few minutes, the carbon nano-structure layer 21 is floated on an acid solution as depicted in FIG. 3(f) which means that the carbon nano-structure layer 21 is ready to be transferred to the sensing part 14 of the optic fiber sensor. Then, the carbon nano-structure layer 21 can be cleaned with distilled water 23 four times or more and can be soaked in the distilled water (DIW) 23.

Thereafter, the sensing part 14 including the exposed core at the predetermined locus of the optic fiber and the carbon nano-structure layer 21 in the container are arranged, so that the sensing part 14 is implanted into the container and coated with or bonded to the carbon nano-structure layer 21 by a dip-coating method (FIG. 3(g)). Then, as an after-treatment, a UV/ozone treatment (or a plasma surface treatment) may be performed to the surface of the sensing part 14 where the carbon nano-structure layer 21 is coated or bonded (FIG. 3(h)).

In accordance with another illustrative embodiment of forming the carbon nano-structure layer 21 on the sensing part 14 of the optic fiber sensor, the carbon nano-structure layer 21 can be bonded to the sensing part 14 of the optic fiber sensor by using a stamper (not illustrated). The carbon nano-structure layer 21 obtained as depicted in FIG. 3(f) is transferred onto the stamper (not illustrated) made of elastomer such as PDMS and a flexible and extensible protective film containing a polymer (elastomer) including porous nano holes may be formed on the carbon nano-structure layer 21 by a photolithography process. Then, after the stamper (not illustrated) and the sensing part 14 to which the stamper (not illustrated) is to be bonded are arranged by using the stamper (not illustrated), the stamper (not illustrated) is pressed onto the sensing part 14 as depicted in FIG. 2(a) or pressed onto the sensing part 14 along its circumference as depicted in FIG. 2(b), and the stamper (not illustrated) is separated from the carbon nano-structure layer 21, so that the sensing part 14 can be coated with or bonded to the carbon nano-structure layer 21. As a result, the carbon nano-structure layer 21 can be transferred to the sensing part 14. Thereafter, the carbon nano-structure layer 21 coated on the sensing part 14 is cleaned with distilled water and dried. The drying process is performed at about 70° C. for about 30 minutes or more, so that bonding strength of the carbon nano-structure layer 21 can be increased. In this way, the optic fiber having the core in which the carbon nano-structure layer 21 is formed at a predetermined locus can be formed. Further, in this way, the sensing part 14 including the optic fiber coated with the carbon nano-structure layer 21 can be manufactured and the optic fiber sensor can be manufactured by positioning the sensing part 14 between the light source and the light detector.

Hereinafter, examples of an optic fiber in which a carbon nano-structure layer is formed, a method of forming the same, and an optic fiber sensor including the optic fiber will be explained in detail with reference to the accompanying drawings, but the present disclosure is not limited thereto.

EXAMPLE 1

In order to manufacture an optic fiber chemical sensor, a light source and a light detector were provided and a sheath of a jacket was removed from a plastic optic fiber by using an appropriate device. The plastic optic fiber manufactured by Mitsubishi Rayon Co., Ltd. was used in this example, a core of the plastic optic fiber made of PMMA had a diameter of about 980/1000 μm, a maximum operating temperature of about 85° C., a bandwidth of about 50 Mhz. 100 m, a bend radius of about 25 mm, and a minimum attenuation of about 650 nm Min, and a FC/APC connector was used as a fiber connector.

After the jacket was removed from the plastic optic fiber, a clad and the core remained. Then, both ends of the plastic optic fiber were planarized with a fine sandpaper sheet. Thereafter, with respect to a predetermined locus to be a sensing part, the clad of the optic fiber was soaked in a solvent containing N,N-dimethylformamide and a piece of clean cloth was used to rub and remove the clad, so that the core at the predetermined locus to be the sensing part was exposed. The exposed core was cleaned with double distilled water and a nitrogen gas. Then, the optic fiber where a graphene layer was to be formed was accommodated in a vacuum chamber, so that additional pollution at the sensing part was prevented. Then, UV/ozone etching process was performed to the sensing part. Thereafter, a pre-prepared graphene layer including a prepared metal catalyst layer was soaked in an iron chloride solution to perform an etching process thereto, so that the graphene layer was separated and floated on a surface of the solution. When the graphene layer was floated, the graphene layer was shifted to a container filled with distilled water and cleaned with the distilled water four times or more. Then, the graphene layer and the sensing part of the optic fiber were arranged in the container accommodating the floated graphene layer to put the optic fiber, so that the graphene layer was transferred onto the sensing part of the optic fiber by a dip-coating method. Thereafter, as an after-treatment, a UV/ozone etching process (70° C. and 3 minutes) was performed to the sensing part and the optic fiber was positioned between the light source and the light detector, so that the optic fiber sensor can be manufactured.

Figure 4B:
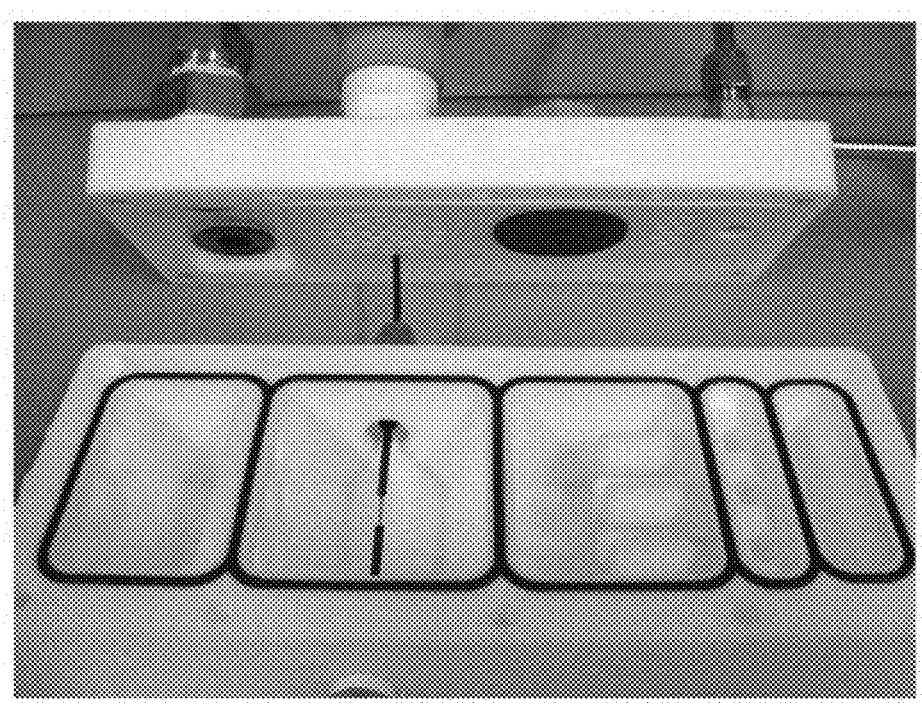
Figure 5:
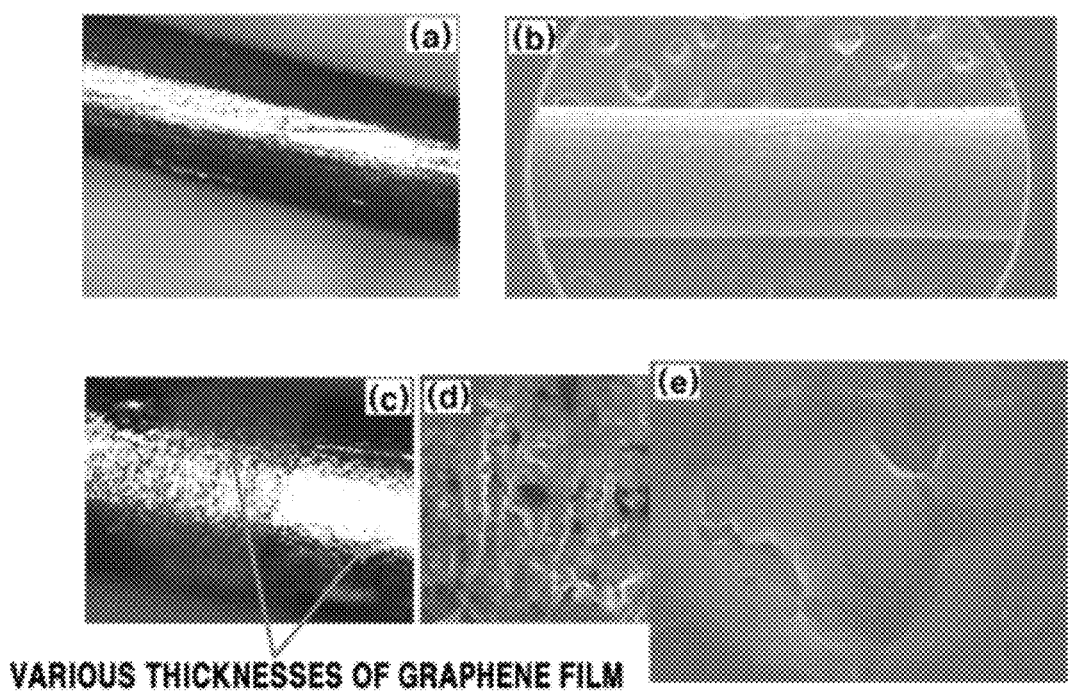
FIG. 5 provides an image of an optic fiber coated with a carbon nano-structure layer by a manufacturing process in accordance with an example of the present disclosure.

FIGS. 4A and 4B provide a schematic view and a image of an experimental system including an optic fiber sensor in accordance with an example of the present disclosure and FIG. 5 provides a image of an optic fiber where a carbon nano-structure layer is formed by a manufacturing process in accordance with an example of the present disclosure.

Figure 6A:
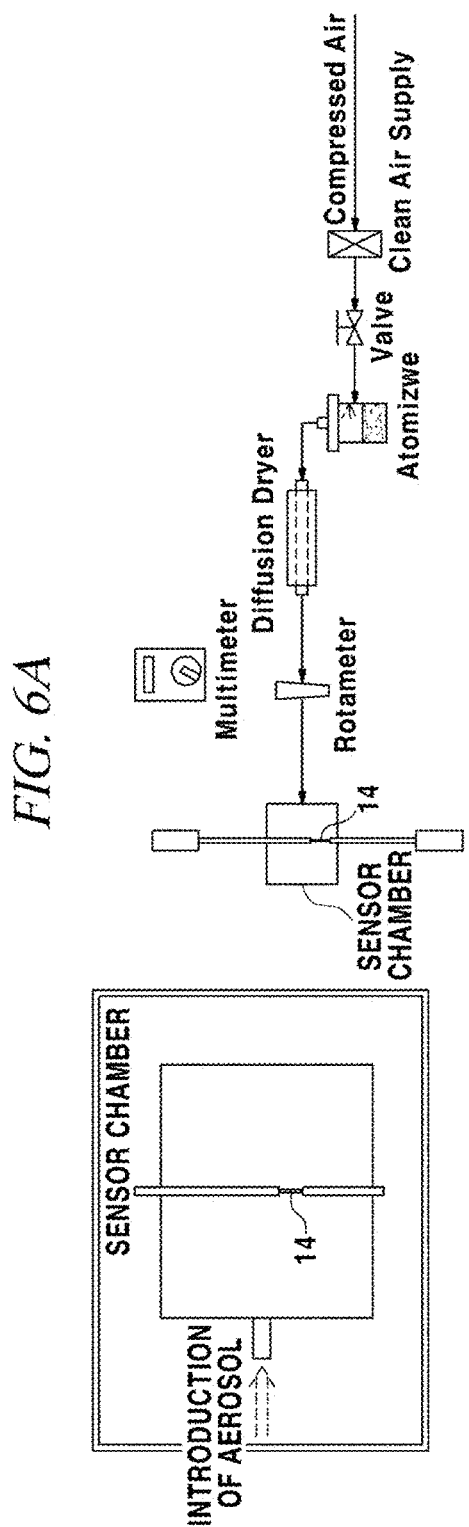
FIGS. 6A, 6B and 6C show a schematic view and an image of an experimental system for detecting various aerosols in accordance with an example of the present disclosure.
Figure 6B:
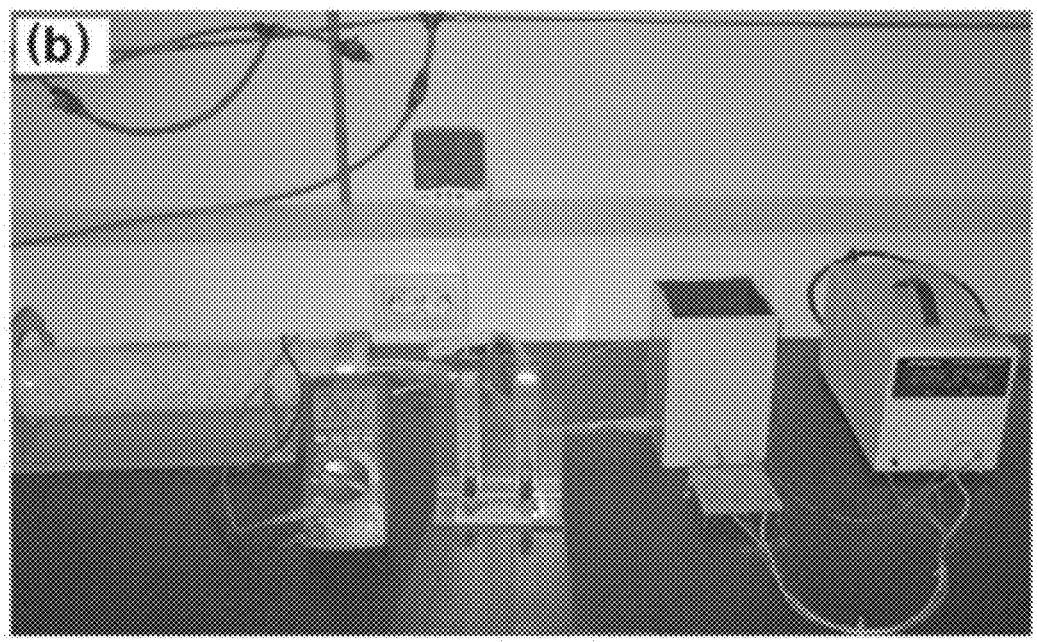
Figure 6C:
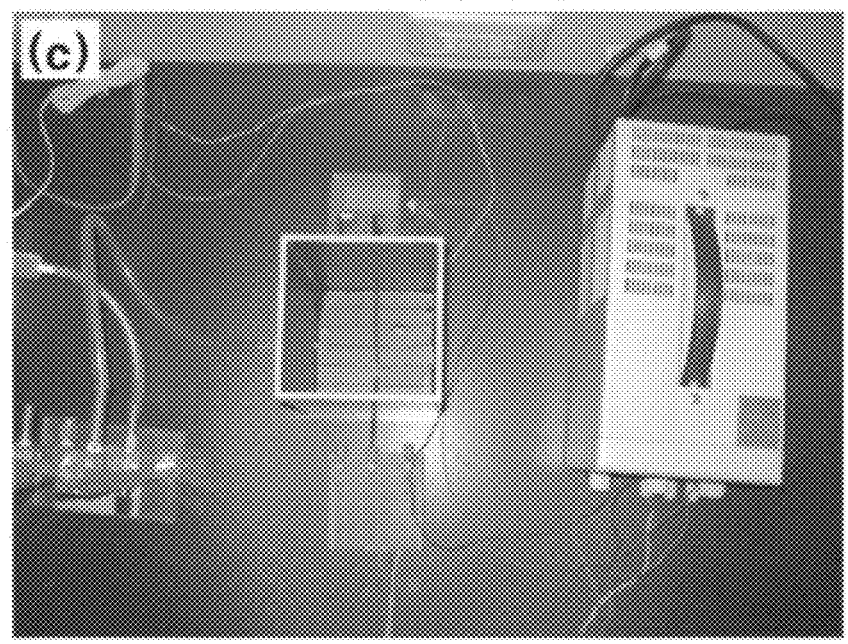
Figure 7A:
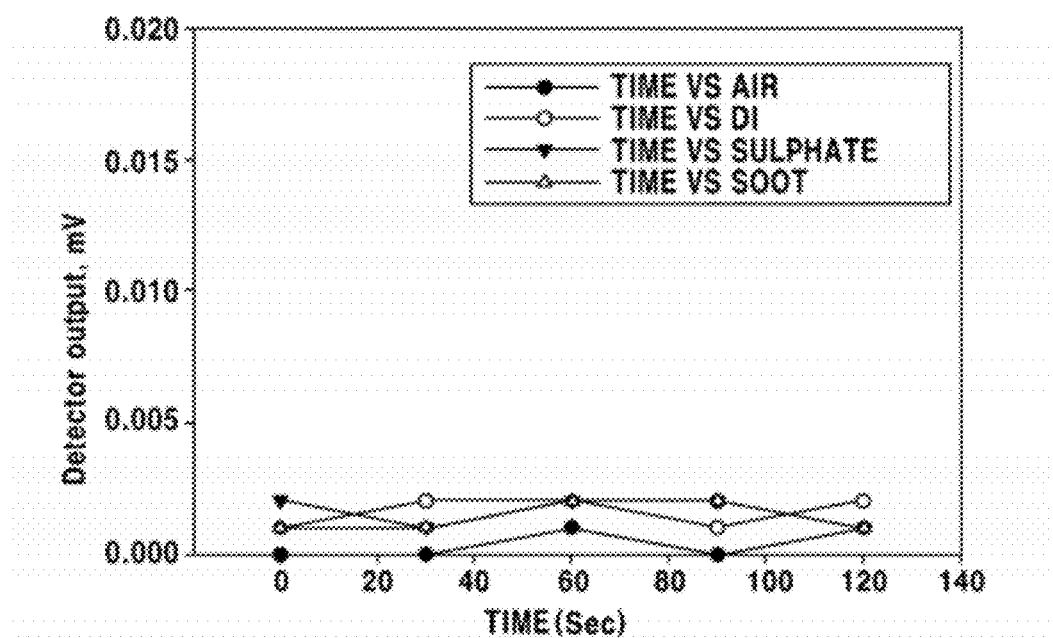
FIGS. 7A and 7B provide graphs showing sensitivity of a conventional optic fiber sensor and an optic fiber sensor in accordance with an example of the present disclosure.
Figure 7B:
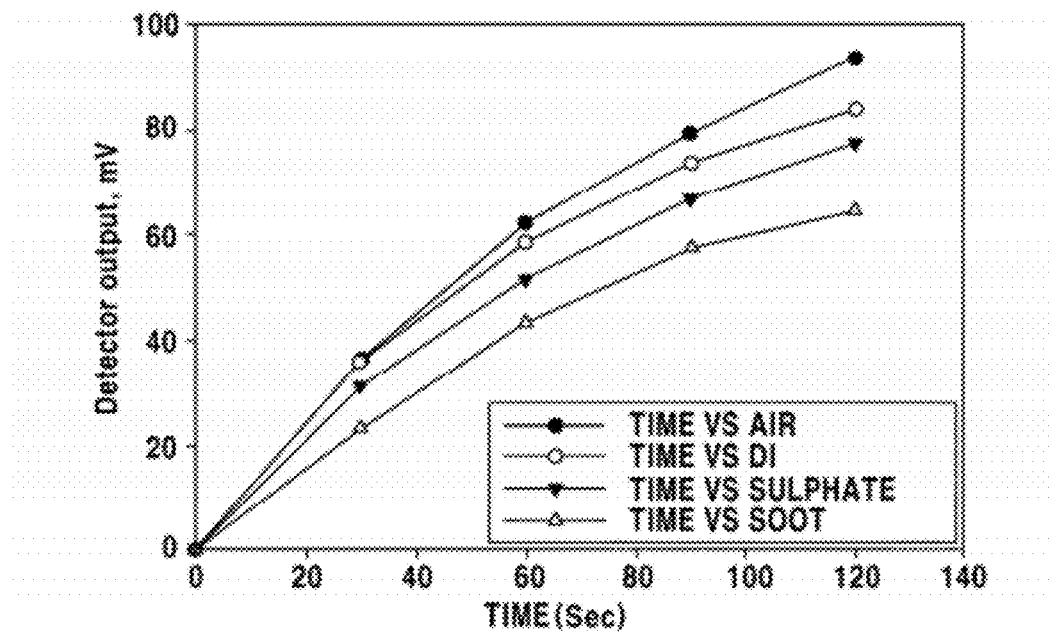

FIGS. 6A, 6B and 6C show a schematic view and a image of an experimental system for detecting various aerosol particles in accordance with an example of the present disclosure and FIGS. 7A and 7B provide graphs showing sensitivity for pollutants of a conventional optic fiber sensor and an optic fiber sensor in accordance with an example of the present disclosure. Referring to FIGS. 7A and 7B, it can be seen that sensitivity of the optic fiber sensor in accordance with an example of the present disclosure is improved as compared with the conventional optic fiber sensor. FIG. 8 provides a graph showing sensitivity for soot when a red light source and a blue light source are individually used in an optic fiber sensor in accordance with an example of the present disclosure.

EXAMPLE 2

Figure 9:
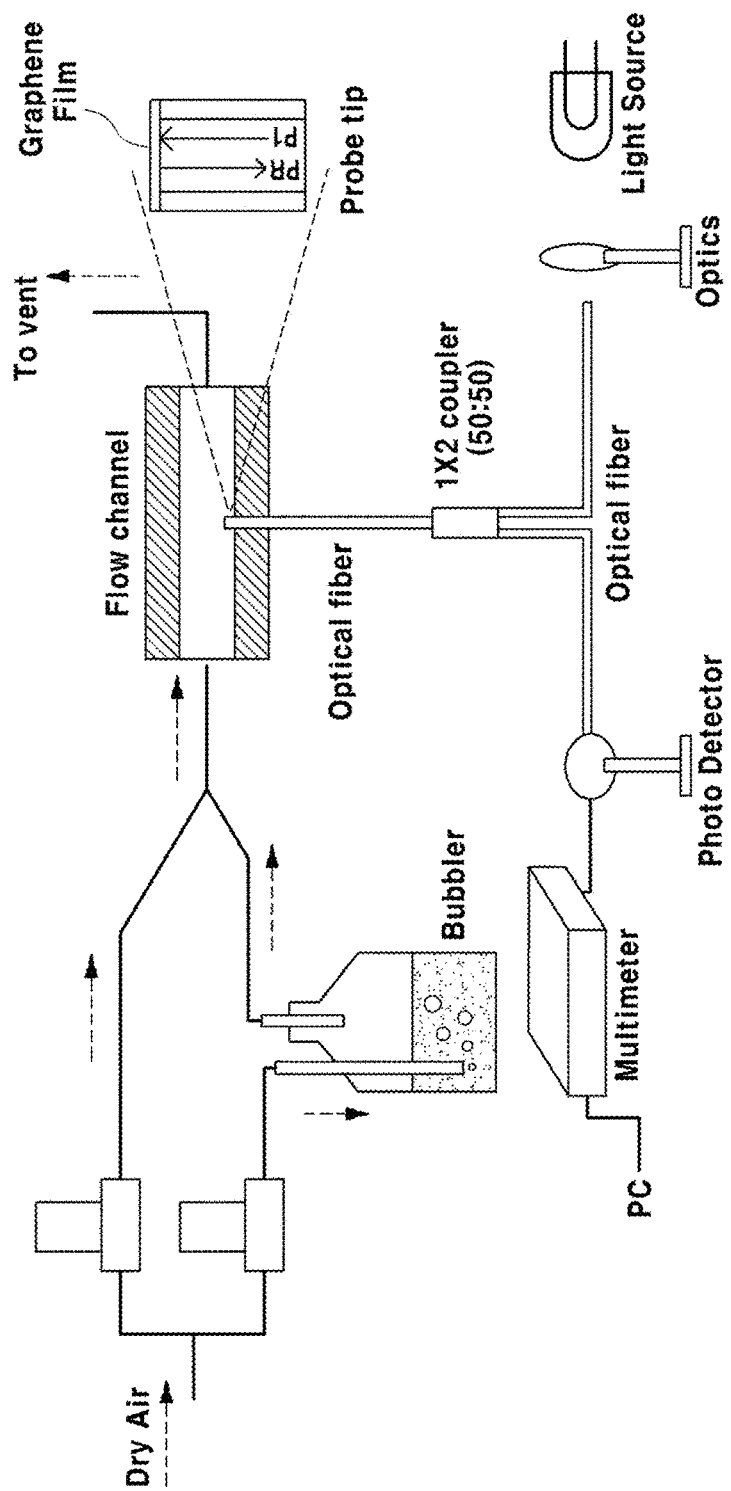
FIG. 9 is a schematic view showing an optic fiber chemical sensor in accordance with an example of the present disclosure.

FIG. 9 is a schematic view showing an experimental system including an optic fiber sensor in accordance with another example of the present disclosure. To be more specific, referring to FIG. 9, a white light source having a wavelength in a range of from about 400 nm to about 800 nm and an output of about 2 mW was used. 1×2 couplers were used for coupling signals reflected from the light source and an interface where sensing of the optic fiber was occurred.

Figure 10:
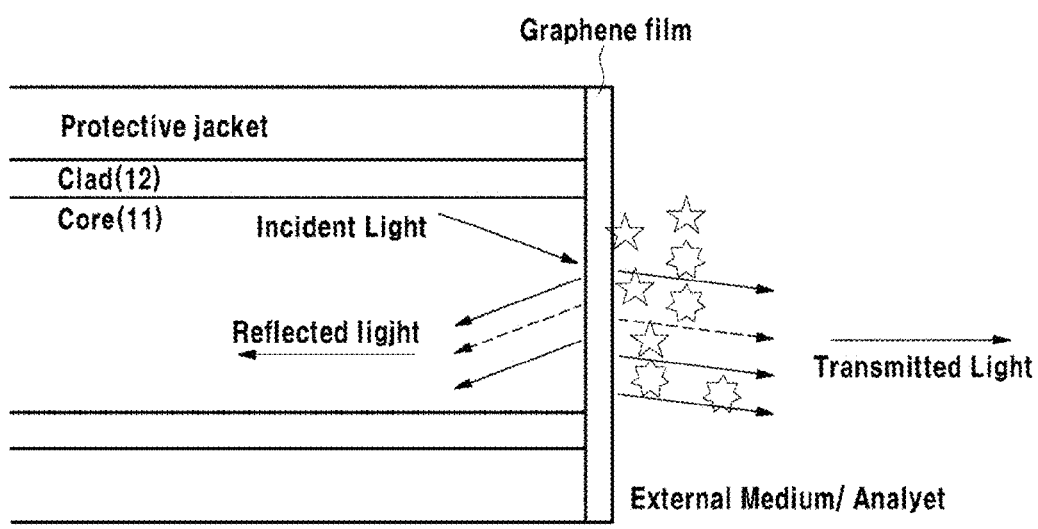
FIG. 10 is a cross sectional view of an optic fiber sensor in accordance with an illustrative embodiment of the present disclosure.

FIG. 10 is an enlarged cross sectional view of the optic fiber used in Example 2. The optic fiber including a clad and a core had a diameter in a range of from about 980 μm to about 1000 μm. In the same manner as Example 1, a graphene layer was formed on an exposed core of the optic fiber and the optic fiber where the graphene layer was formed was positioned on a floating channel (having a diameter of about 10 mm to about 70 mm).

A result sensed by the optic fiber was observed by a light detector. As the light detector, a Si photodiode light detector (Thorlab, PDA36A) capable of observing a wavelength range from about 350 nm to about 1100 nm was used. In addition, a multimeter (Keithley, 2700) was equipped.

As a reference gas, a compressed dry air was used. As a material to be sensed, an acetone gas was used. The acetone gas was generated through a bubbling method in a constant temperature flask and the acetone gas in various concentrations was introduced onto the floating channel including the optic fiber. A flow rate of a total gas including the dry air and the acetone gas was kept at about 1000 ml/min by controlling with a gas flow rate measurement device. The above-described process was performed at room temperature.

Figure 11A:
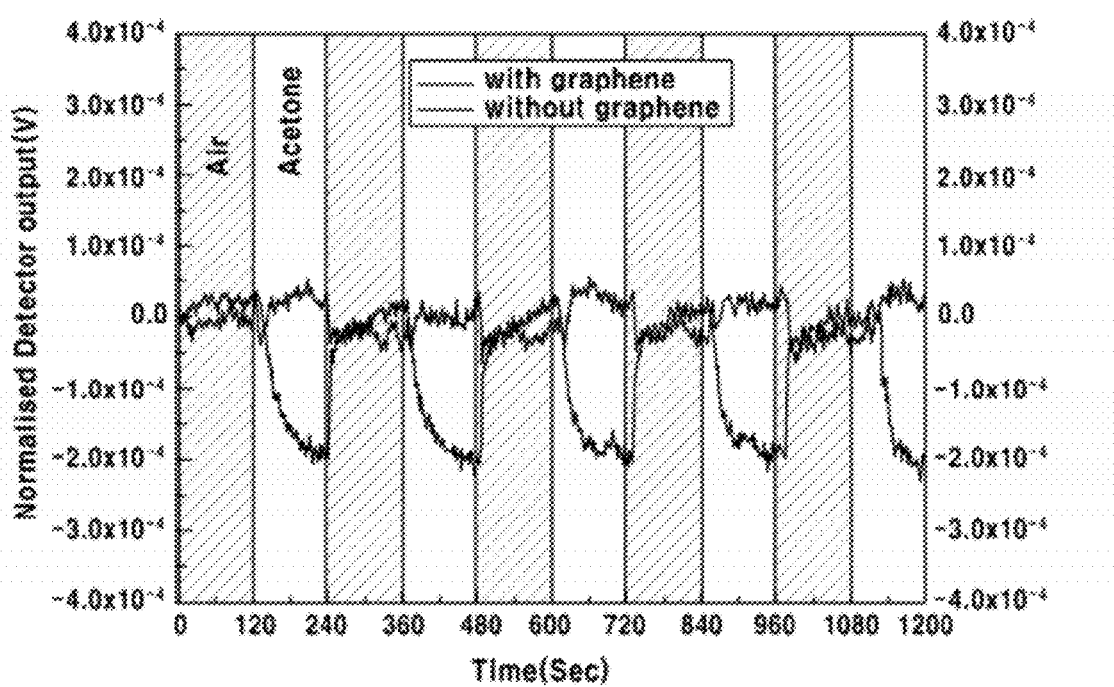
FIGS. 11A and 11B provide graphs showing a result of sensing an acetone gas by using an optic fiber chemical sensor in accordance with an example of the present disclosure.
Figure 11B:
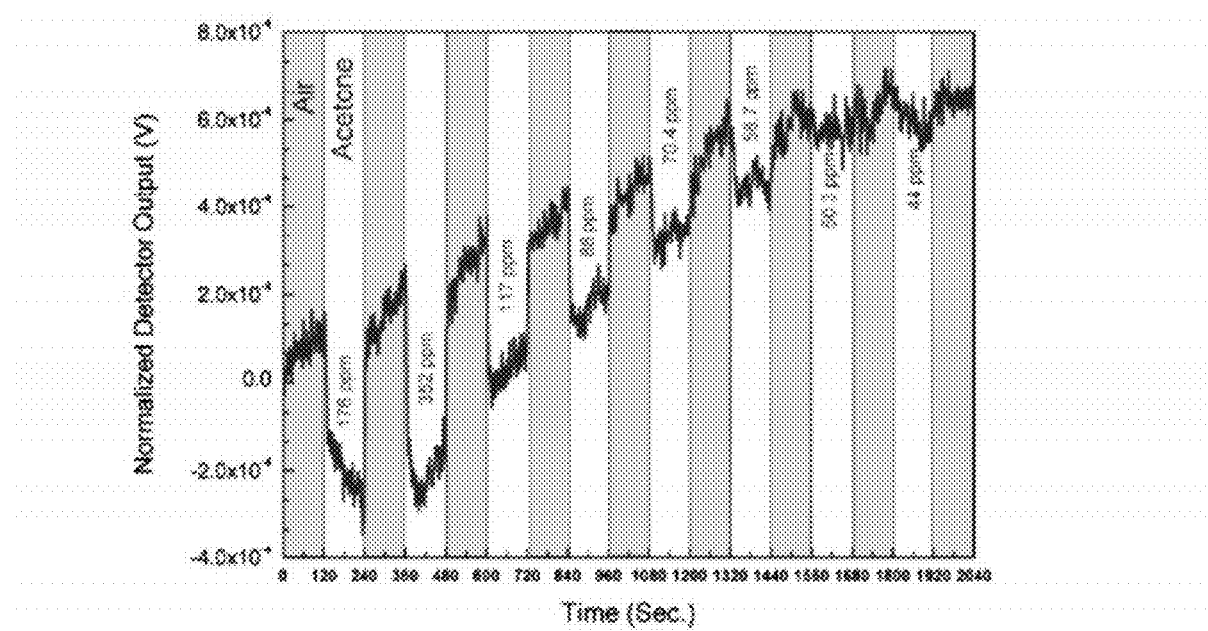

FIG. 11A is a graph as a result of observing an acetone gas by using an optic fiber sensor including a graphene layer formed in accordance with Example 2 and an optic fiber sensor without a graphene layer. As can be seen from the graph, if there is formed a graphene layer on an optic fiber, sensitivity is greatly increased. FIG. 11B is a graph showing a change in output of an optic fiber chemical sensor with an acetone gas having different concentrations in a range of from about 44 ppm to about 352 ppm. Referring to the graph, as a concentration of the acetone gas is decreased, a change in output of the sensor is decreased.

The examples are provided to explain the present disclosure, but the present disclosure is not limited to the above-described examples and can be modified in various ways. It is clear that the present disclosure can be modified in various ways by those skilled in the art within a scope of the present disclosure.

What is claimed is:

1. An optic fiber, comprising a layer formed in contact with a circumferential surface of a core at a predetermined locus of the optic fiber,
    wherein the layer consists of a planar graphene layer, and
    wherein a refractive index at an interface between the core and the planar graphene layer is modulated in presence of adsorbents on the surface of the planar graphene layer.

2. The optic fiber of claim 1, wherein the core of the optic fiber comprises one or more materials selected from the group consisting of glass, plastic, and a polymer.

3. The optic fiber of claim 1, wherein the optic fiber includes a multimode optic fiber.

4. The optic fiber of claim 1, further comprising a protective film formed on the planar graphene layer.

5. The optic fiber of claim 1, wherein the surface of the core at the predetermined locus of the optic fiber is either a flat surface or a curved surface.

6. An optic fiber chemical sensor comprising an optic fiber of claim 1, wherein a sensing part in the optic fiber chemical sensor comprises the planar graphene layer formed on the core at the predetermined locus of the optic fiber.

7. The optic fiber chemical sensor of claim 6, further comprising:
    a light source;
    a light detector; and
    the optic fiber of claim 1 positioned between the light source and the light detector.

8. The optic fiber chemical sensor of claim 6, wherein the sensor is configured to detect a target material to be sensed in a gas, liquid or particle state.

9. The optic fiber chemical sensor of claim 6, wherein the sensor is configured to detect a target material to be sensed by using a change in a surface refractive index of the planar graphene layer included in the sensing part caused by adsorption of a gas, a liquid or a particle.

10. A method for forming an optic fiber chemical sensor including the optic fiber of claim 1, the method comprising:
removing a sheath and a jacket from the predetermined locus of the optic fiber to expose the core of the optic fiber;
forming a sensing part including the planar graphene layer on the exposed core at the predetermined locus of the optic fiber; and
positioning the optic fiber comprising the sensing part between a light source and a light detector.

11. The optic fiber of claim 1, wherein the exposed surface of the core is a flat surface or a curved surface; and
the planar graphene layer has a flat surface or a curved surface with a degree of curvature substantially corresponding to the exposed surface of the core.

12. The optic fiber of claim 1, wherein the exposed surface of the core is a curved surface; and
the planar graphene layer wraps around the curved surface of the core of the optic fiber.

13. A method for forming a planar graphene layer on a core of an optic fiber, the method comprising:
removing a sheath and a jacket from a predetermined locus of the optic fiber to expose a circumferential surface of the core of the optic fiber; and
forming the layer on the exposed circumferential surface of the core of the optic fiber,
wherein the layer consists of a planar graphene layer, and
wherein a refractive index at an interface between the core and the planar graphene layer is modulated in presence of adsorbents on the surface of the planar graphene layer.

14. The method of claim 13, comprising:
floating the planar graphene layer on a surface of distilled water; and
contacting the exposed core of the optic fiber with the floated planar graphene layer to transfer the floated planar graphene layer onto the exposed core.

15. The method of claim 14, further comprising:
surface-treating the exposed core of the optic fiber with ultra-violet light or plasma.

16. The method of claim 13, comprising:
floating the planar graphene layer on a surface of distilled water;
transferring the planar graphene layer onto a stamper containing an elastomer; and
pressing the planar graphene layer transferred onto the stamper to the exposed core of the optic fiber to transfer the planar graphene layer onto the exposed core.

17. The method of claim 16, wherein the exposed core is coated with the planar graphene layer by pressing the stamper along a circumference of the exposed core.

18. The method of claim 13, wherein the core of the optic fiber comprises one or more materials selected from the group consisting of glass, plastic, and a polymer.

19. The method of claim 13, wherein a graphene layer formed by chemical vapor deposition with controlling its area and thickness is used as the planar graphene layer.

20. The method of claim 13, further comprising:
forming a protective film on the planar graphene layer.

21. The method of claim 13, wherein the core at the predetermined locus of the optic fiber has a flat surface or a curved surface.

22. An optic fiber, comprising:
a core disposed in a sheath; and
a layer consisting a graphene layer,
wherein the sheath is removed at a predetermined locus of the optic fiber to expose a circumferential surface of the core of the optic fiber, and
wherein the graphene layer is disposed on the exposed circumferential surface of the core such that a refractive index at an interface between the core and the graphene layer is modulated in presence of adsorbents on a surface of the graphene layer.

* * * * *